(12) United States Patent
Roth et al.

(10) Patent No.: US 12,064,148 B2
(45) Date of Patent: Aug. 20, 2024

(54) BONE ANCHOR, INSTRUMENTS, AND METHODS FOR USE

(71) Applicant: MIRUS LLC, Marietta, GA (US)

(72) Inventors: Noah Roth, Marietta, GA (US); Wayne Gray, Marietta, GA (US); Kevin R. Strauss, Marietta, GA (US); Ryan O'Flaherty, Marietta, GA (US); Clint Walker, Marietta, GA (US); Antonio Terrell, Marietta, GA (US)

(73) Assignee: MIRUS LLC, Marietta, GA (US)

( * ) Notice: Subject to any disclaimer, the term of this patent is extended or adjusted under 35 U.S.C. 154(b) by 130 days.

(21) Appl. No.: 17/666,278

(22) Filed: Feb. 7, 2022

(65) Prior Publication Data

US 2022/0168025 A1 Jun. 2, 2022

Related U.S. Application Data

(63) Continuation of application No. 16/333,062, filed as application No. PCT/US2017/051985 on Sep. 18, 2017, now abandoned.
(Continued)

(51) Int. Cl.
*A61B 17/70* (2006.01)
*A61B 17/80* (2006.01)
(Continued)

(52) U.S. Cl.
CPC .......... *A61B 17/7083* (2013.01); *A61B 17/70* (2013.01); *A61B 17/7035* (2013.01);
(Continued)

(58) Field of Classification Search
None
See application file for complete search history.

(56) References Cited

U.S. PATENT DOCUMENTS

| 5,653,709 A | 8/1997 | Frigg |
| 6,132,432 A | 10/2000 | Richelsoph |

(Continued)

FOREIGN PATENT DOCUMENTS

| WO | 2017/003926 | 1/2017 |
| WO | 2018/053388 | 3/2018 |

OTHER PUBLICATIONS

International Search Report and Written Opinion, issued in International Application No. PCT/US2017/051985, dated Nov. 17, 2017, 9 pages.
(Continued)

*Primary Examiner* — Jan Christopher L Merene
(74) *Attorney, Agent, or Firm* — UB Greensfelder LLP; Brian Erkin Turung (57) ABSTRACT

Disclosed herein is a surgical instrument configured for attachment to a surgical device. The surgical instrument includes a distal region having a curved internal surface configured to mate with a curved external surface of the surgical device, a rotational locking feature that limits rotational movement of the instrument with respect to the surgical device, and an axial locking feature that limits axial movement of the blade with respect to the surgical device. Methods of using the surgical instruments include sliding the axial locking feature past a corresponding axial locking feature on the surgical device, locking the axial locking feature to the corresponding axial locking feature on the surgical device (thereby limiting axial movement of the elongated blade with respect to the surgical device), adjusting the position of the surgical device using the surgical instrument, and disengaging the axial locking feature (for example, by using a disengagement instrument).

7 Claims, 11 Drawing Sheets

Related U.S. Application Data (60) Provisional application No. 62/395,656, filed on Sep. 16, 2016.

(51) Int. Cl.
*A61B 17/86* (2006.01)
*A61F 2/44* (2006.01)

(52) U.S. Cl.
CPC .......... *A61B 17/7076* (2013.01); *A61B 17/80* (2013.01); *A61B 17/863* (2013.01); *A61B 17/864* (2013.01); *A61F 2/44* (2013.01)

(56) References Cited

U.S. PATENT DOCUMENTS

| | | | |
|---|---|---|---|
| 7,488,444 B2 | 2/2009 | Furst et al. | |
| 7,699,876 B2 | 4/2010 | Barry et al. | |
| 8,337,530 B2 | 12/2012 | Hestad et al. | |
| 8,974,501 B2 | 3/2015 | Dikeman | |
| 9,179,937 B2 | 11/2015 | Iott et al. | |
| 9,198,698 B1* | 12/2015 | Doose | A61B 17/7011 |
| 9,277,942 B2 | 3/2016 | Biedermann et al. | |
| 9,345,516 B2 | 5/2016 | Biedermann et al. | |
| 10,888,356 B2 | 1/2021 | Beyer | |
| 2004/0138662 A1 | 7/2004 | Landry | |
| 2007/0083213 A1 | 4/2007 | Siravo et al. | |
| 2008/0108992 A1 | 5/2008 | Barry et al. | |
| 2009/0171391 A1* | 7/2009 | Hutton | A61B 17/8861 606/301 |
| 2009/0228055 A1 | 9/2009 | Jackson | |
| 2011/0263945 A1 | 10/2011 | Peterson | |
| 2012/0089142 A1 | 4/2012 | Mullaney et al. | |
| 2013/0261679 A1 | 10/2013 | McBride | |
| 2015/0039035 A1 | 2/2015 | Kruger | |
| 2015/0066042 A1 | 3/2015 | Cummins | |
| 2015/0088210 A1 | 3/2015 | Reitblat | |
| 2016/0051384 A1 | 2/2016 | Patel | |
| 2016/0089186 A1 | 3/2016 | Beyer | |
| 2016/0237541 A1 | 8/2016 | Patel et al. | |
| 2017/0143379 A1 | 5/2017 | Walker | |
| 2017/0164980 A1 | 6/2017 | Le Roux | |
| 2018/0008318 A1 | 1/2018 | Fiechter | |
| 2019/0262044 A1* | 8/2019 | Roth | A61B 17/70 |

OTHER PUBLICATIONS

International Preliminary Report on Patentability issued in International Application No. PCT/US2017/051985, dated Mar. 28, 2019, 7 pages.

* cited by examiner

BONE ANCHOR, INSTRUMENTS, AND METHODS FOR USE

RELATED APPLICATIONS

This application claims the benefit of U.S. Non-Provisional patent application Ser. No. 16/333,062, file on Mar. 13, 2019, which is a National Stage Application filed under 35 U.S.C. § 371 of PCT/US2017/051985, filed Sep. 18, 2017, which claims the benefit of priority to U.S. Provisional Application No. 62/395,656, filed Sep. 16, 2016, which is hereby incorporated by reference in its entirety.

FIELD

The bone anchor and methods of use disclosed herein pertain to the field of orthopedic surgery, and more specifically, spinal surgery.

BACKGROUND

Spinal fusion is a common surgical procedure used to correct numerous disease states including degenerative disorders, trauma, instability, and deformity. A frequent method of fusion entails the use of bone screws placed through various sections of the vertebral body including the body, pedicle, facets, lamina, lateral masses, and/or transverse processes. These screws are then linked rigidly with a rod, plate or other fixation device to immobilize the vertebral segments.

Due to the variation in a patient's anatomy and differences in screw placement technique, screws are often not perfectly aligned which makes securement of a spinal rod more difficult. To solve this, many screws that have a threaded shank portion incorporate an articulating tulip or receiver connected to the proximal end of the shank portion, such as in a polyaxial or multi-axial bone screw. Polyaxial bone screws allow for a variation in the angulation of the tulip/receiver relative to the shank portion in order to allow the tulip/receiver to more closely align for receiving a fixation device such as a fixation rod within the tulip/receiver. Some bone screws allow for the lateral translation of the tulip/receiver relative to its point of fixation. Further alignment may be accomplished by contouring of the spinal rod itself to compensate for any remaining misalignment. For example, if a spinal rod is employed, the rod can be bent to conform to the patient anatomy and location of the tulip/receiver to securely attach thereto.

While developments to decrease the overall invasiveness of spinal surgical methods are desirable, conventional surgeries still utilize certain invasive steps, such as tapping or undertapping. A tapping procedure is performed as follows: a bone access needle is used to generate an access hole in the bone. The inner shaft of the bone access needle is removed, and a guidewire is inserted a guidewire thru the inner hole of the bone needle. The remaining portion of the bone access needle is removed while taking care to ensure the guidewire does not move within the bone. A small diameter tap is inserted by rotating the tap into the bone. The smallest diameter tap is removed by turning it outwardly, and a slightly larger size tap is inserted and removed in the same fashion to widen the hole. The taps get progressively larger until the hole is the appropriate for the bone anchor. Undertapping procedures are similar to tapping procedures, except that the last tap used is slightly smaller in diameter than the actual bone anchor. Tapping and undertapping procedures lengthen the duration of the surgery. Conventional spinal surgeries also utilize relatively bulky devices. Developments to decrease the overall invasiveness of spinal surgical methods are therefore needed.

SUMMARY

The instruments and devices described below remedy some of the aforementioned discrepancies in the field of spinal surgery. The elongated blades disclosed herein are configured to attach to a surgical device, such as a bone anchor. Two blades can be used together to create a path through the patient's skin and to the surgical instrument. An exemplary elongated blade includes a distal region having a curved internal surface that is configured to mate with a curved external surface of the surgical device, a rotational locking feature on the curved internal surface that limits rotational movement of the blade with respect to the surgical device, and an axial locking feature on the curved internal surface that limits axial movement of the blade with respect to the surgical device. The blade is curved in at least one transverse cross-section. the walls of the blade are from 1 millimeters to 4 millimeters. In some embodiments, the blade is formed of molybdenum rhenium (MoRe).

In some embodiments, the rotational locking feature includes one or more longitudinally extending protrusions. The longitudinally extending protrusion can include angled longitudinally extending surfaces, or it can be substantially cylindrical. In some embodiments, the longitudinally extending protrusion comprises at least one flat proximal or distal surface.

In some embodiments, the axial locking feature comprises a laterally extending ridge. The laterally extending ridge can be positioned at a distal portion of a living hinge. The living hinge can be an elongated tab cut into a sidewall of the distal region of the blade. In some embodiments, the laterally extending ridge can include angled surfaces. For example, the proximal surface of the laterally extending ridge can create an acute angle with a sidewall of the living hinge in at least one longitudinal cross section, and/or the distal surface of the laterally extending ridge can create an obtuse angle with the sidewall of the living hinge in at least one longitudinal cross section.

A proximal region of the blade can include at least one fixation feature configured to be attached to one or more surgical instruments. The fixation features can be, for example, thru-holes, thru-slots, notches, grooves, cut-outs, or a combination thereof. The proximal region can also include a permanent or non-permanent connection to the proximal region of a second elongated blade. As a pair, the first and second elongated blades, which attach to the same surgical device, create a path for surgical access to the device.

Methods of using the elongated blades are also disclosed herein. The methods include: sliding the axial locking feature of the elongated blade past a corresponding axial locking feature on the surgical device, locking the axial locking feature of the elongated blade to the corresponding axial locking feature on the surgical device, thereby limiting axial movement of the elongated blade with respect to the surgical device, adjusting the position of the surgical device using the elongated blade, and disengaging the axial locking feature (using a disengagement instrument, for example). In some embodiments of the method, sliding the axial locking feature of the elongated blade past a corresponding axial locking feature on the surgical device includes flexing a living hinge outwardly from the surface of the elongated blade, and returning the living hinge to its original position after sliding the axial locking feature of the elongated blade past the corresponding axial locking feature on the surgical device. In some embodiments of the method, locking the axial locking feature of the elongated blade to the corresponding axial locking feature on the surgical device further includes engaging angled surfaces of the axial locking feature of the elongated blade to complementary angled surfaces of the axial locking feature of the surgical device. Some embodiments of the method also include sliding the rotational locking feature of the elongated blade into or onto a complementary rotational locking feature on the surgical device. In some embodiments, the disengagement instrument comprises a projecting member that pushes the axial locking feature away from the surgical device.

DETAILED DESCRIPTION

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" are orientations that indicate the positioning of a surgical device. As used herein, the terms "distal" and "distally" indicate a direction farther from a practitioner performing a surgical procedure. "Proximal" and "proximally" indicate a direction closer to a practitioner performing the procedure. For example, the shank of a bone anchor is distal to the ball head of an anchor.

Figure 1:
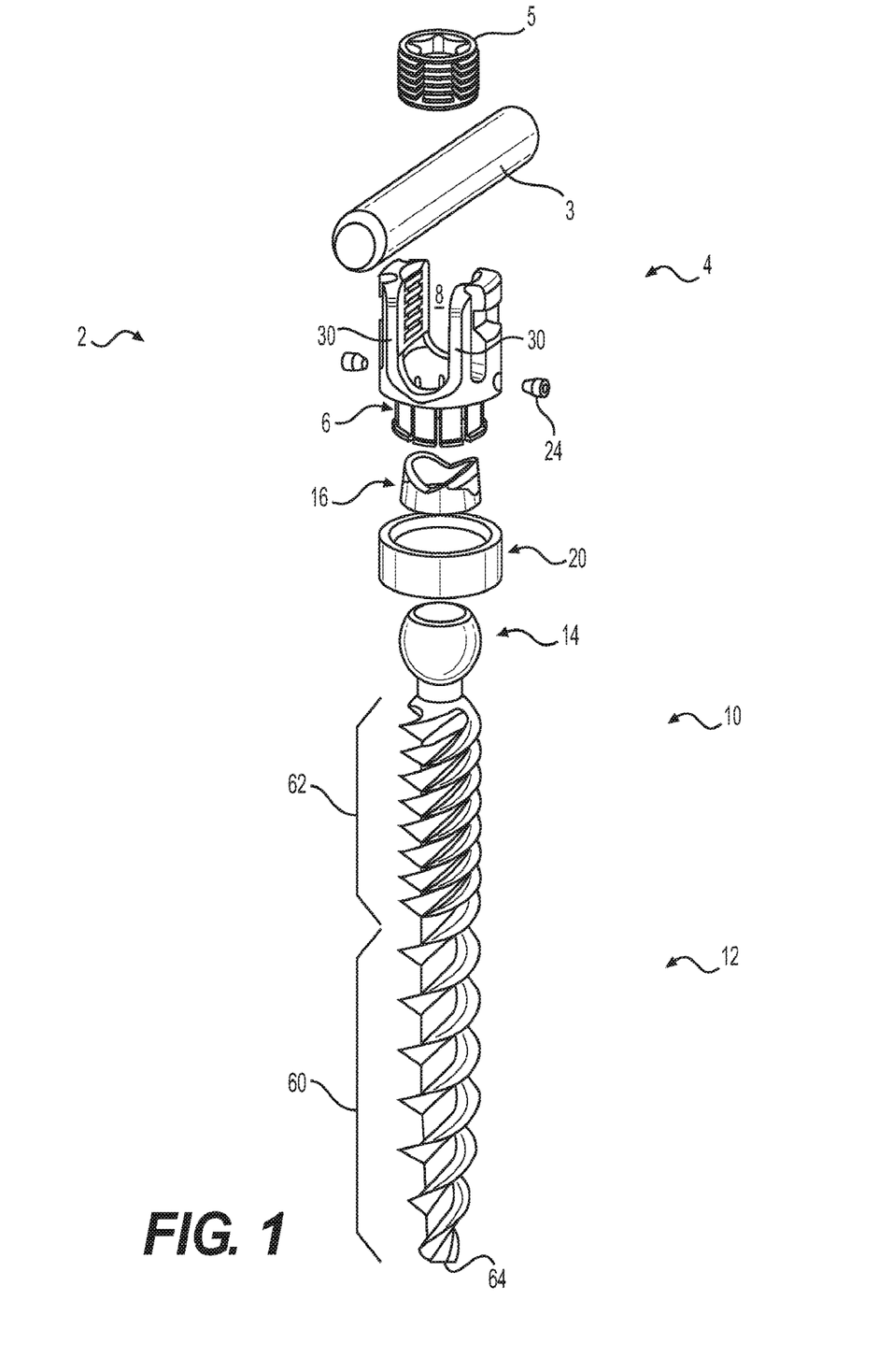
FIG. 1 is an exploded perspective view of one embodiment of a bone anchor and spinal rod.
Figure 2:
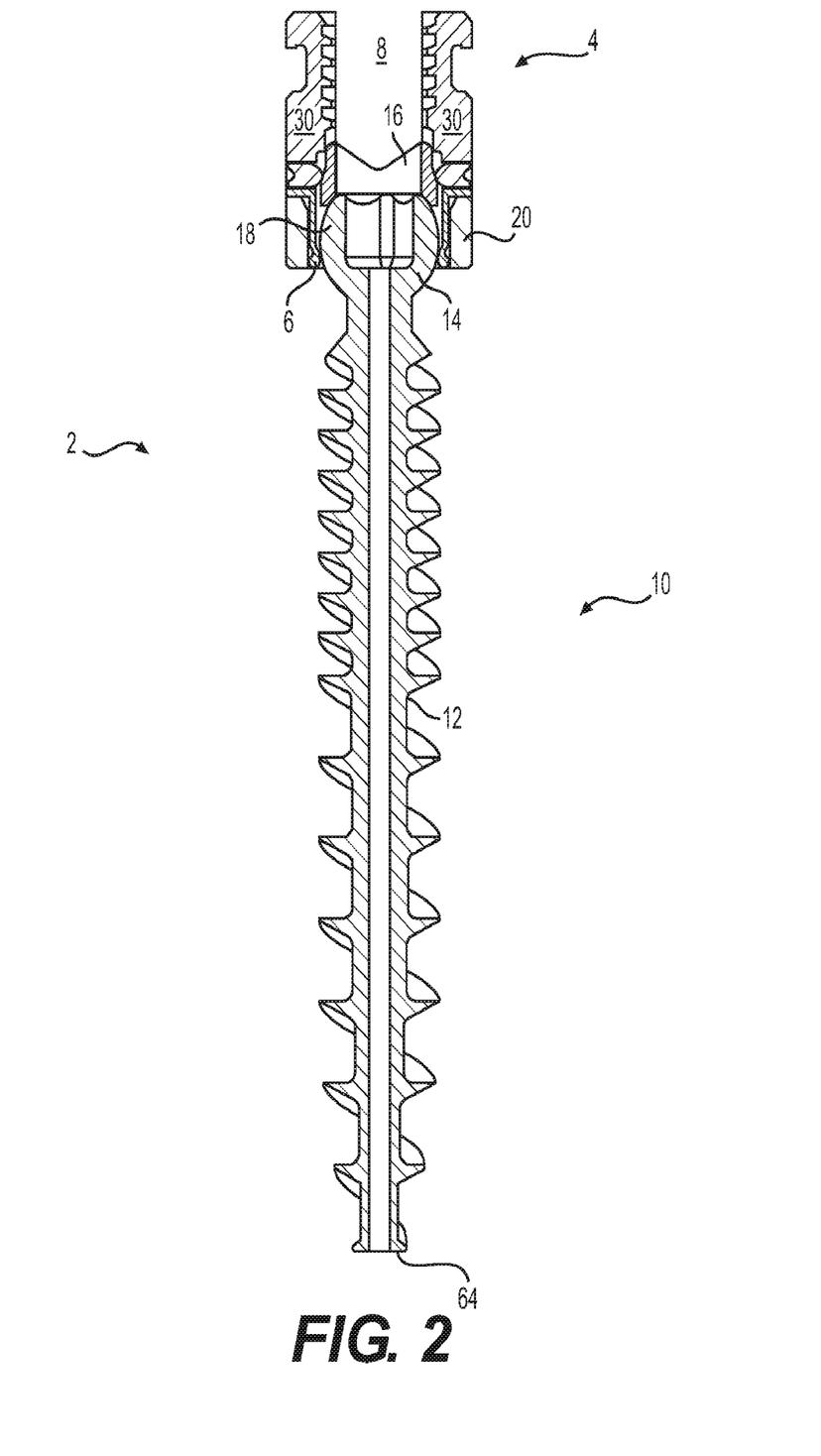
FIG. 2 is a side cross-sectional view of the bone anchor of FIG. 1.

FIG. 1 shows an exploded perspective view of one embodiment of a bone anchor 2. FIG. 2 shows a side cross sectional view of the embodiment shown in FIG. 1. The bone anchor 2 includes a tulip housing 4 having a through hole 8 and a distal radially expandable portion 6. The tulip housing 4 captures the ball head 14 of threaded shank 10, creating a polyaxial feature. Particularly, the ball head 14 is positioned within through hole 8 of the distal radially expandable portion 6 of the tulip housing 4. The bone anchor 2 further includes a pressure cap 16. The pressure cap 16 is also positioned within the through hole 8, proximally adjacent to the ball head 14. The distal end of the pressure cap 16 includes a bearing surface 18 for interfacing with the ball head 14, creating a ball and socket device. Bone anchor 2 further includes a retaining ring 20 which limits radial expansion of the radially expandable portion 6. This limitation of radial expansion prevents movement of the pressure cap 16 and the proximal ball head 14 out of the through hole 8. The bone anchor 2 is used in conjunction with a spinal rod 3, which is placed between the sidewalls 30 of the tulip housing 4 and locked into place with a set screw/locking cap 5. The set screw/locking cap 5 forces the spinal rod 3 against the pressure cap 16 and the pressure cap 16 against the ball head 14, which is prevented from being pushed out of the bottom of the tulip housing 4 by the retaining ring 20 positioned around the distal radially expandable portion 6. The shank 10 also includes a distal threaded portion 12 for inserting into the bone.

Figure 3:
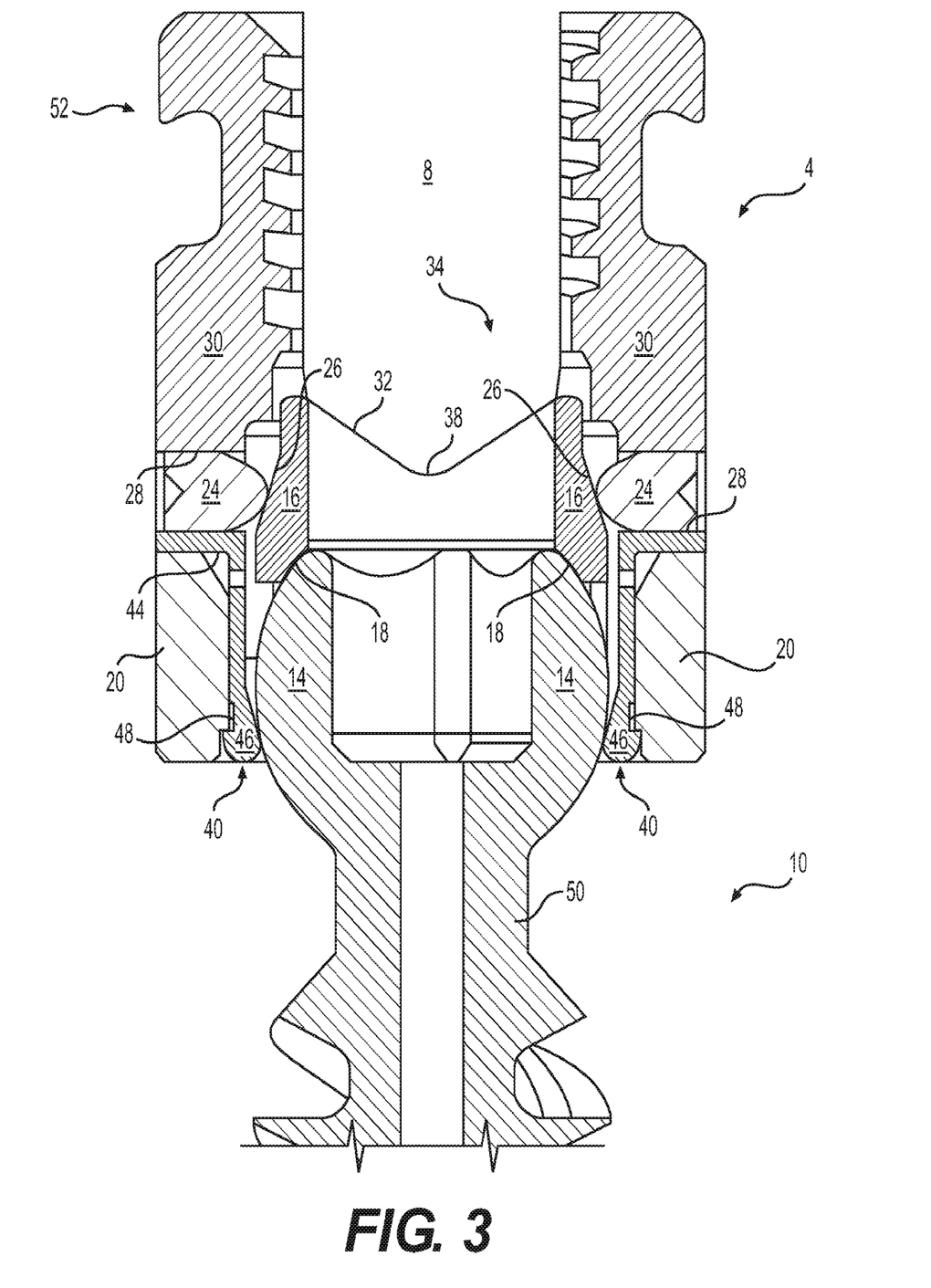
FIG. 3 is an enlarged view of the proximal region of the bone anchor and tulip housing of FIG. 1.

FIG. 3 shows an enlarged cross-sectional view of a proximal portion of one embodiment of a bone anchor 2. The bone anchor 2 includes a compression mechanism for bringing the pressure cap 16 into close contact with ball head 14, creating a friction fit that increases the amount of force needed to manipulate the tulip housing 4. The compression mechanism can include a compressing component 24 that exerts a distally oriented force onto the pressure cap 16. In the embodiment shown in FIG. 3, the compressing component 24 is a pin that extends through a hole 28 in the sidewall 30 of the tulip housing 4. The compressing component 24 exerts a lateral force onto a ramped surface 26 of pressure cap 16. The lateral force is translated to a distally oriented force by the ramped surface 26, limiting proximal movement of the pressure cap 16 and the proximal ball head 14 within the through hole 8. The compression mechanism is not limited to the embodiment shown. For example, the compression mechanism could include other types of compressing components, including, but not limited to, screws, springs, or wedges.

Figure 4:
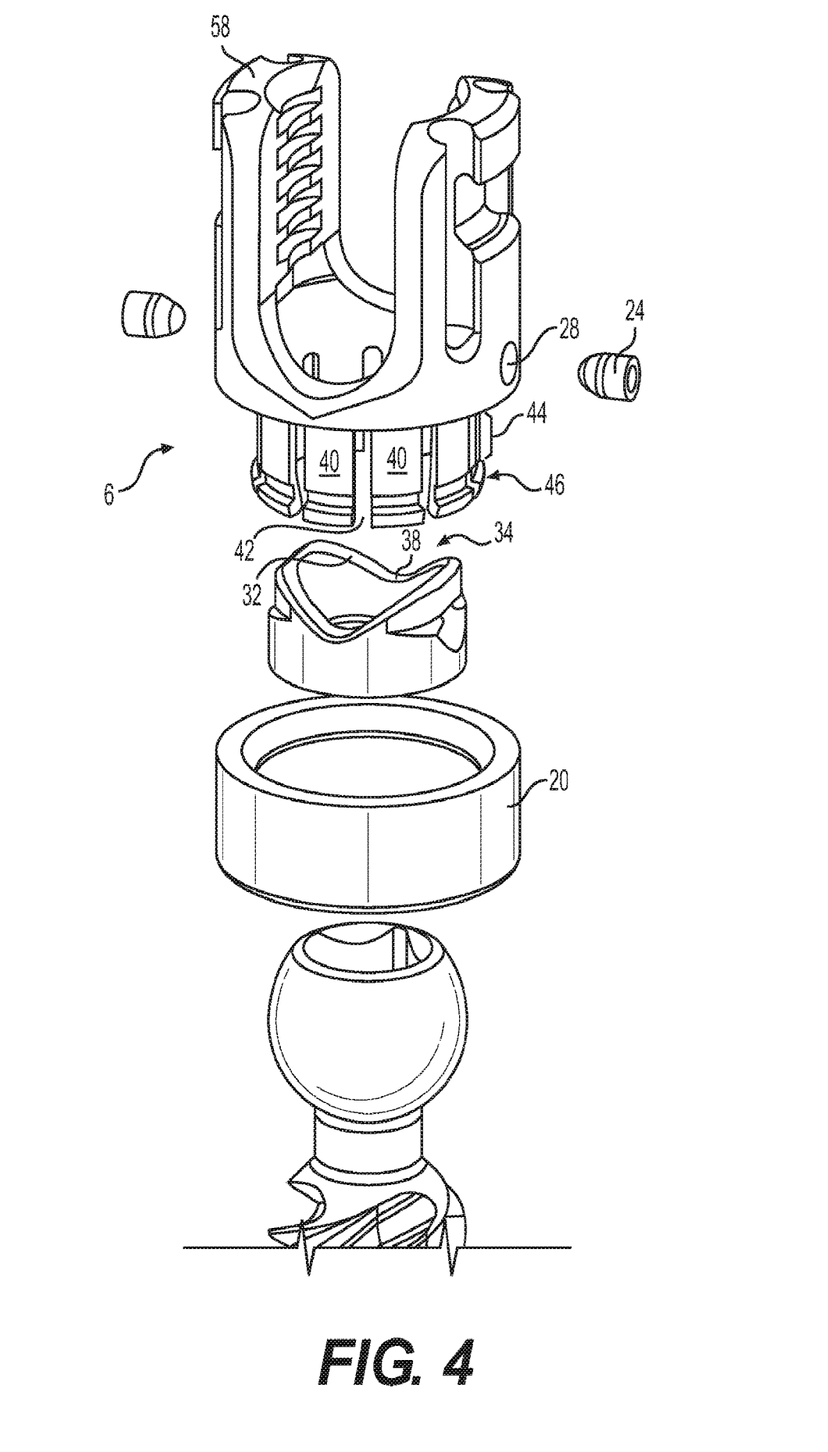
FIG. 4 is an enlarged exploded perspective view of the proximal region of the bone anchor of FIG. 1.

FIG. 4 shows an enlarged exploded view of the proximal tulip housing 4 seen first in FIG. 1. As shown in FIGS. 3 and 4, the proximal surface 32 of the pressure cap 16 narrows to create a saddle 34 for spinal rod 3. The saddle 34 shown in the embodiment of FIGS. 3 and 4 is substantially V-shaped in cross section, widening as it extends in a proximal direction. The V-shape advantageously enables the bone anchor 2 to accept spinal rods 3 of different diameters. For example, the saddle 34 can accept spinal rods 3 that range from about 3.5 millimeters to about 4.5 millimeters in diameter, including about 3.5 millimeters, about 3.6 millimeters, about 3.7 millimeters, about 3.8 millimeters, about 3.9 millimeters, about 4.0 millimeters, about 4.1 millimeters, about 4.2 millimeters, about 4.3 millimeters, about 4.4 millimeters, and about 4.5 millimeters. Other sizes of spinal rods 3 are also contemplated. The substantially V-shaped saddle 34 can be rounded at its narrowest, distal-most location 38, or it can narrow to a point at its distal-most location 38. The concave bearing surface 18 of pressure cap 16 can be shaped to center ball head 14. For example, in the embodiment shown in FIG. 3, bearing surface 18 takes a frustoconical shape. In other embodiments, bearing surface 18 could be, for example, conical or semispherical.

Tulip housing 4 includes a distally located radially expandable portion 6. The radially expandable portion 6 expands to enable the insertion of the pressure cap 16 and the ball head 14 into the through hole 8, despite their larger diameters (discussed in greater detail below). The embodiment shown in FIG. 4, for example, includes multiple tabs 40 separated by relief slots 42. The tabs 40 flex outwardly to allow pressure cap 16 and ball head 14 to be pushed proximally through the distal end of the radially expandable portion 6. The pressure cap 16 and ball head 14 are then translated proximally within the through hole 8, creating a space at the distal end of the through hole 8. The external retaining ring 20 is then positioned over the outside of radially expandable portion 6, causing it to radially contract. With the external retaining ring 20 in place within the lateral groove 44 around the outside of the radially expandable portion 6 (see FIG. 3), the pressure cap 16 and ball head 14 are translated distally to their final position. Lateral groove 44 is bounded at its distal end by a laterally extending locking feature 46 positioned near the distal end of radially expandable portion 6. The laterally extending locking feature 46 of radially expandable portion 6 mates with a corresponding laterally extending locking feature 48 on the retaining ring 20 to prevent its displacement.

When the radially expandable portion 6 is in an expanded state, the smallest inner diameter of the radially expandable portion 6 is larger than the largest outer diameter of the ball head 14, enabling passage of the ball head 14 for a bottom-up assembly. However, when radially expandable portion 6 is in a contracted state (due to the constriction by the retaining ring 20), the same smallest inner diameter is smaller than the largest outer diameter of the ball head 14, which prevents it from being expelled distally from the tulip housing 4. In other words, retaining ring 20 prevents the radially expandable portion 6 from expanding, and the assembly remains intact. With the ball head 14 captured, for example, having from about a 0.0001 inch to about a 0.04 inch lateral interference, maximum angulation of the threaded shank 10 is achieved. The conical angulation can be, for example, up to 75 degrees (from about 0 degrees to about 75 degrees). Angulation is dependent on the diameter of the ball head 14, the diameter of the neck 50, the diameter of the through hole 8, and the amount of material on the underside of the tulip housing (adjacent the through hole 8).

The proximal portion 52 of the tulip housing 4 has a smallest inner diameter that is smaller than the largest outer diameters of the ball head 14, the pressure cap 16, and the threads of the threaded shank 10, preventing these items from being proximally translated within the through hole 8. The bottom-up assembly (wherein the pressure cap 16 and ball head 14 are inserted into the tulip housing 4 through the distal end of the through hole 8) is advantageous because it allows the tulip housing 4 to be smaller and therefore less invasive. In some embodiments, the tulip housing 4 can be from about 5% to about 15% smaller than conventionally used tulip housings. The diameter of ball head 14 (as well as most major diameter sizes of the bone anchor) is larger than the narrowest path through the tulip housing 4, so it is not possible to assemble from the top as with conventional bone anchors and polyaxial screws. In one embodiment, the largest outer diameter of the tulip housing 4 is from about 9.9 millimeters to about 11.9 millimeters.

Figure 5:
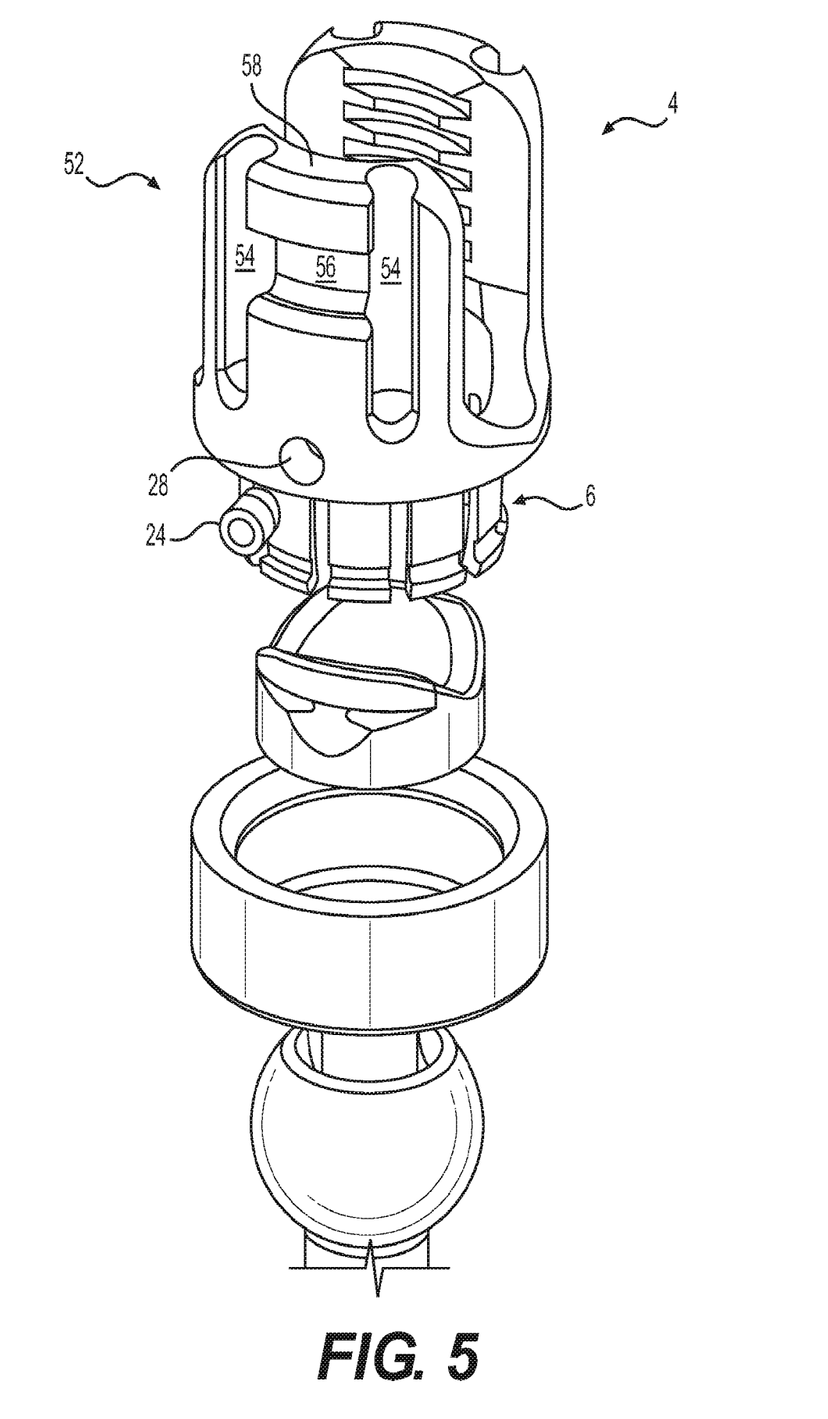
FIG. 5 is an enlarged exploded perspective view of the proximal region of the bone anchor of FIG. 1, rotated to show the attachment features on the external surface of the tulip housing.

The tulip housing 4 can include attachment features that assist with engagement to other devices, such as one or more blades (e.g., blades 66, 68 shown in FIG. 8) and/or other surgical instruments (such as, for example, rod reduction instruments, instruments to compress the screws/vertebral body onto an interbody device, and/or instruments to distract the screws/vertebral body for nerve decompression prior to locking the rod in place). The tulip housing 4 can include a plurality of longitudinally extending indentations 54. For example, the tulip housing 4 can include four longitudinally extending indentations 54, with two indentations 54 being arranged on each sidewall 30 of the tulip housing 54 (as in the embodiment shown in FIG. 5). The longitudinally extending indentations 54 can be silo-shaped, and can limit rotational and translational forces when mated to longitudinally extending protrusions on an engaged instrument. This disclosure contemplates that the tulip housing 4 can include more or less than four longitudinally extending indentations 54, which are provided only as an example in some of the figures. Alternatively, the tulip housing 4 could include one or more longitudinally extending protrusions that limit rotational forces when mated to longitudinally extending indentations on an engaged instrument. The longitudinally extending protrusions can be positioned circumferentially around the external surface of the tulip housing. In the embodiment shown in FIG. 5, each longitudinally extending indentation 54 has a curved longitudinally extending surface. The indentations 54 break through the external surface of the tulip housing 4 such that in a cross-sectional view, less than a 360-degree circle is formed by the external surface of tulip housing 4. In other embodiments, a longitudinally extending indentation 54 can have multiple longitudinally extending surfaces that meet each other at angles. The tulip housing 4 can also include attachment features that resist axial forces, such as the laterally extending indentation 56, or undercut lip, shown in FIG. 5. The laterally extending indentation 56 is positioned distally from the proximal-most surface 58 of the tulip housing 4, and is configured to mate with laterally extending protrusions on an engaged instrument. Alternatively, the tulip housing 4 could include laterally extending protrusions that limit axial forces when mated to laterally extending indentations on an engaged instrument. The surfaces of the laterally extending indentations or protrusions can be rounded or angled.

Some or all of the components of the bone anchor 2 can be formed of a metal material. For example, in some embodiments the tulip housing 4, shank 10, pressure cap 16, retaining ring 20, and/or pins 24 are formed of molybdenum rhenium (MoRe). The use of MoRe in surgical implants is described elsewhere, for example, in International Patent Application Publication No. WO 2017/003926, published Jan. 5, 2017, and entitled "Molybdenum alloys for medical devices", U.S. Patent Application Publication No. 2016/0237541, published Aug. 18, 2016, and entitled "Improved Metal Alloy For Medical Devices", and U.S. Pat. No. 7,488,444 to Furst et al., issued Feb. 10, 2009, and entitled "Metal alloys for medical devices", which are incorporated by reference in its entirety and for all purposes.

The use of MoRe enables the design of smaller, less invasive components. MoRe as a material is highly resistant to fatigue, which enables the design of thinner walls. MoRe is not notch sensitive, which enables the design of notches and angled surfaces. The notches enable, for example, the inclusion of tabs 40 that lend flexibility of the radially expanding portion 6. Angled surfaces can be advantageous, for example, to prevent sliding between interlocking mechanisms (such as sliding between the interlocking features 46, 48 on the radially expanding portion 6 and retaining ring 20, or sliding between the indentations 56, 58 on tulip housing 4 and their counterparts on engaged instruments). Angled corners also take up less space than rounded corners, which again enables the design of smaller devices.

Figure 6:
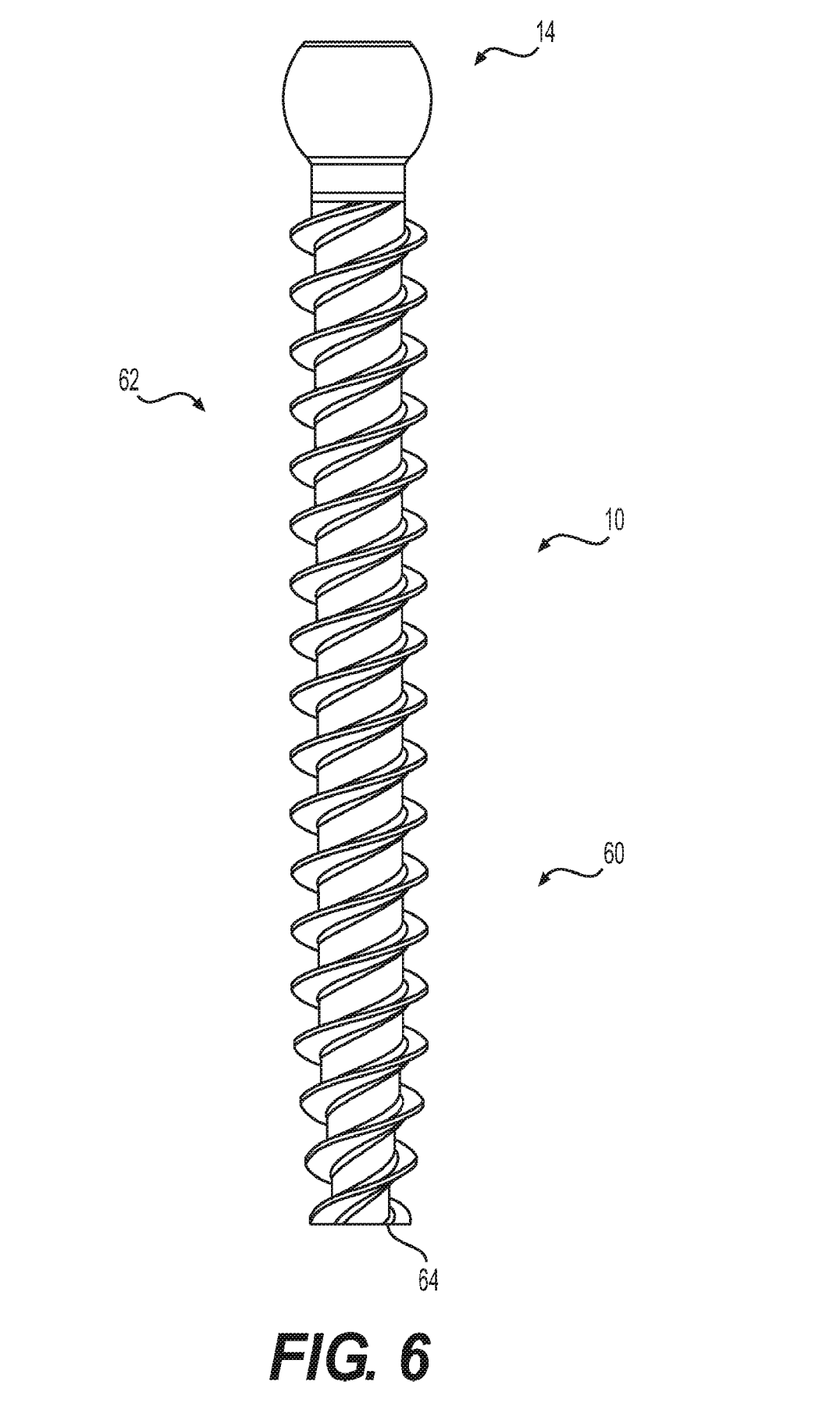
FIG. 6 is a side view of a threaded shank.
Figure 7:
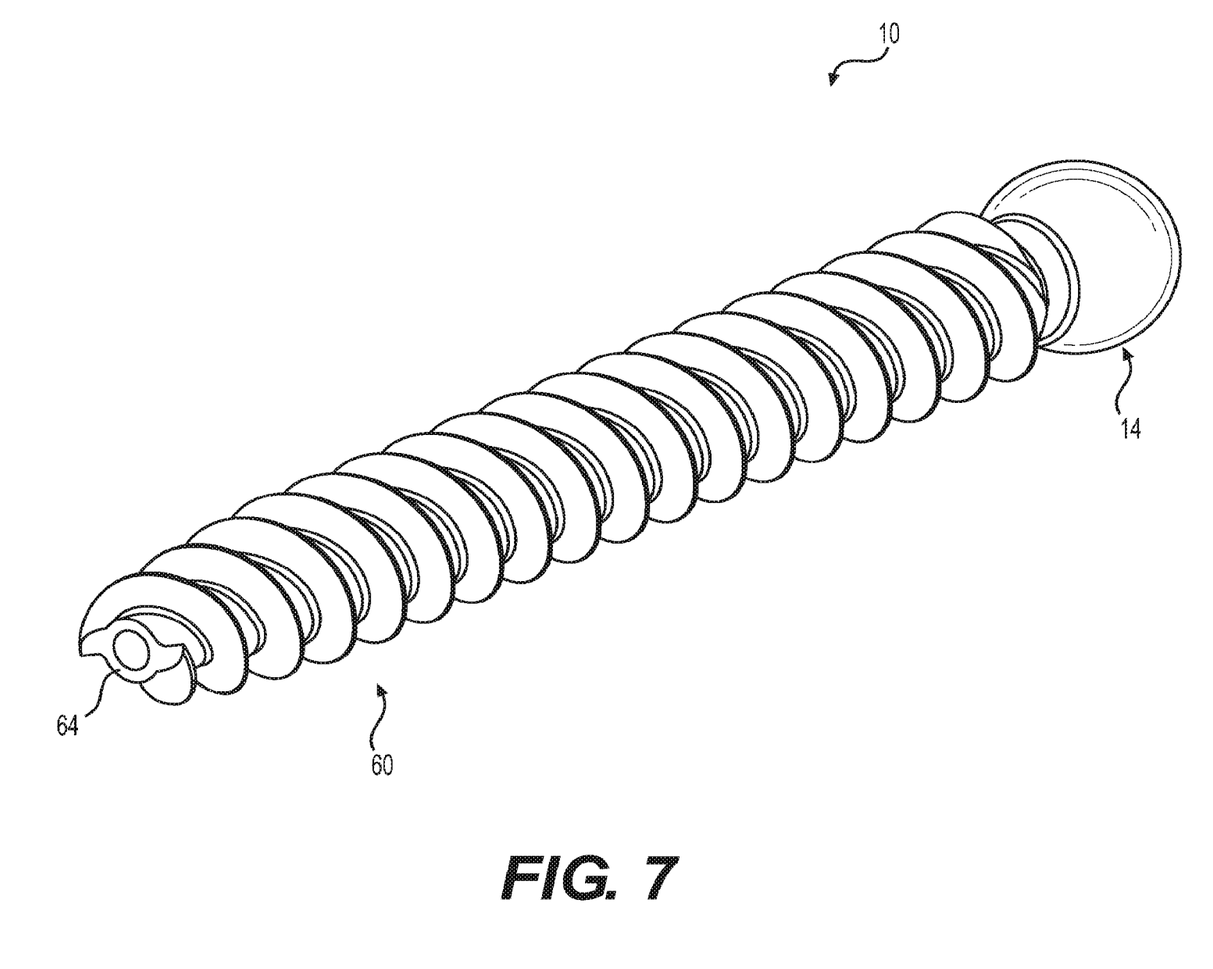
FIG. 7 is a perspective view of the threaded shank shown in FIG. 6.

Various embodiments of the shank 10 are shown in FIGS. 1 and 6. FIG. 7 shows a perspective view of the shank 10 shown in FIG. 6. The embodiments shown in FIGS. 1 and 6 include a distal threaded portion 12 having a distal set of threads 60 that cut into bone as the screw is rotated. The distal set of threads 60 extends to meet the distal end 64 of the shank 10 (i.e., the channel depth of the distal set of threads 60 at the distal end 64 of shank 10 is greater than zero), and can terminate with a cutting edge. In the embodiment shown in FIG. 1, the distal threaded portion 12 includes a proximal set of threads 62 with a pitch that is smaller than the pitch of the distal set of threads 60. The proximal set of threads 62 are a quad lead and the distal set of threads 60 are a dual lead. The proximal set of threads 62 can extend distally for at least 10 millimeters. In the embodiment shown in FIG. 6, the distal and proximal sets of threads 60, 62 have equivalent pitch and lead. The pitch is therefore constant throughout the threaded region. The threaded region is dual lead. The major and minor diameters of the threaded region of the threaded shank 10 narrow as they approach distal end 64 of the shank 10. This narrowing maintains an equal distance between the major and minor diameter of the screw thread, which improves thread pullout and provides consistent bone engagement for the entirety of the screw thread. The minor diameter of the distal threaded portion 12 can be sized to create the greatest flank overlap and surface area in order to maximize purchase and pullout strength. In some embodiments, the minor diameter is cylindrical in cross-section. The minor diameter, depending on major diameter, can be sized to match standard gauge needle diameters (which is often the first step of a spinal procedure). Alternatively, a drill, awl, or probe could be used to create the initial hole. In doing so, the bone anchor is capable of being used without the need to tap or undertap, a common procedural step. In one embodiment, only a pilot hole, which matches the minor diameter of the threaded shank, is necessary for bone anchor insertion.

Figure 8:
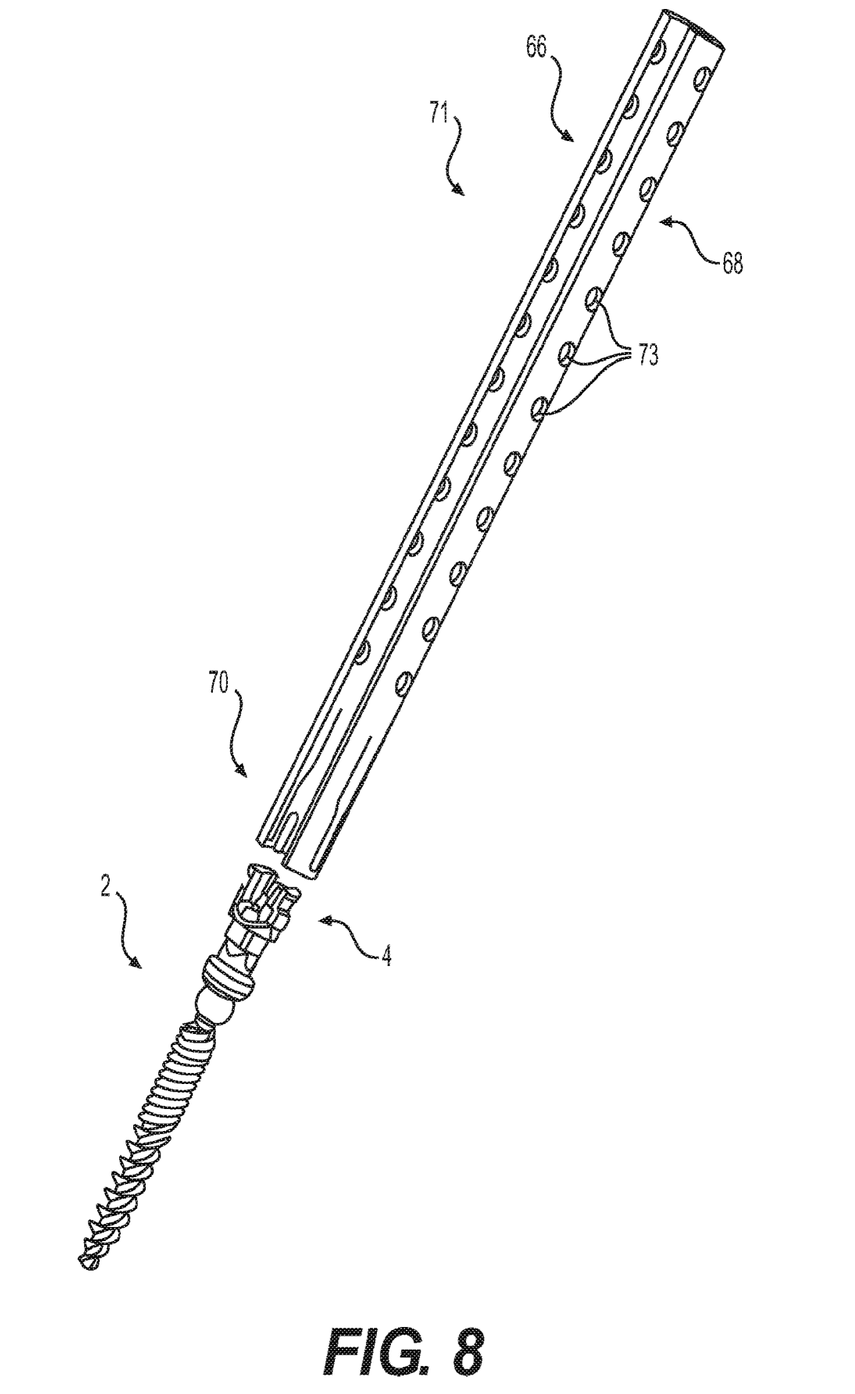
FIG. 8 is a perspective view of a bone anchor and a pair of blades.

Instruments for use with a bone anchor are also disclosed herein. FIG. 8 shows an exploded perspective view of bone anchor 2 with first and second blades 66, 68. Blades 66, 68 are partially curved, thin walled members. The blades are configured to be attached to the bone anchor 2 before or during a surgical procedure, and detached at the end of the surgical procedure. FIG. 8 shows the use of a pair of blades, but in some embodiments, a single blade can be joined to a bone anchor 2, or more than two blades can be joined to a bone anchor 2. During a procedure, blades attach to tulip housing 4 and extend proximally away from the spine and above the surface of the skin, providing a channel for surgical access and enabling manipulation of tulip housing 4. A pair of blades, such as the pair 66, 68, can be joined at a proximal region 71 via a permanent or non-permanent connection positioned between the two blades (not shown).

Adjacent pairs of blades define a path between adjacent bone anchors 2 along the spine of the patient during the surgery (not shown). A longitudinal member, such as a spinal rod 3, can be passed or threaded between one pair of blades 66, 68 and an adjacent pair of blades along the spine. The proximal regions 71 of the blades 66, 68 can include fixation features 73, such as through-holes, through-slots, notches, grooves, or cut-outs, for attachment to other surgical instruments. The blades can be made of disposable or reusable materials. Materials used to make blades 66, 68 can include but are not limited to: MoRe, stainless steel, polypropylene, polycarbonate, titanium or a titanium alloy, carbon fiber, and aluminum. In some embodiments, the walls of the blades range from about 1 millimeter to about 4 millimeters.

Figure 9:
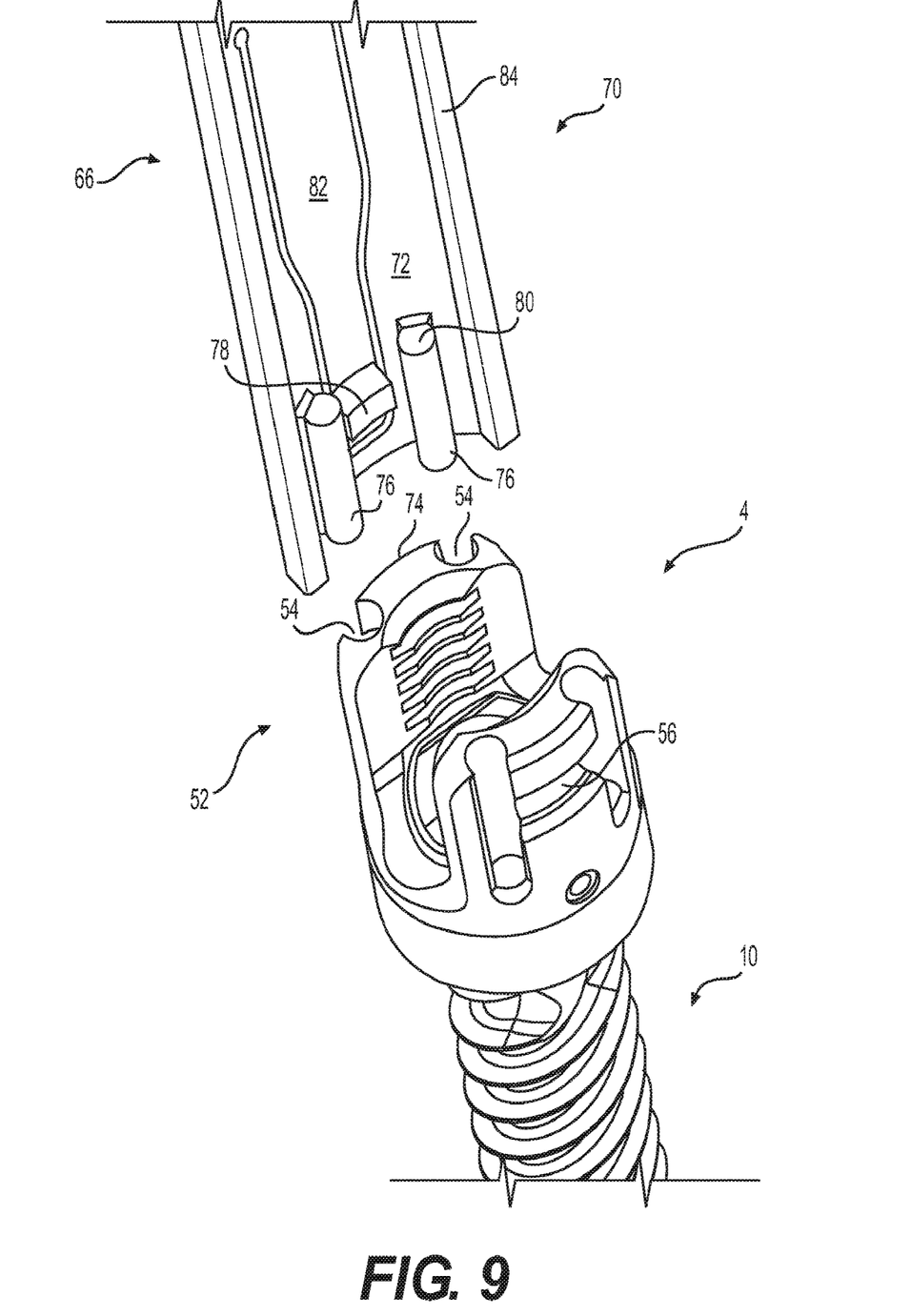
FIG. 9 is a perspective view of a bone anchor and the distal region of a blade.

FIG. 9 shows an enlarged view of distal region 70 of the embodiment of blade 66 seen in FIG. 8. Distal region 70 has a curved internal surface 72 that is configured to mate with the curved external surface 74 of tulip housing 4. For example, the curved internal surface 72 includes rotational locking features 76 (which limit rotational movement of the blade with respect to the bone anchor) and an axial locking feature 78 (that limits axial movement of the blade with respect to the surgical device). The rotational locking features 76 can be, for example, one or more longitudinally extending protrusions, or silos, configured to mate with the longitudinally extending indentations 54 on the proximal region 52 of tulip housing 4, described above. During a procedure, the blade 66 slides distally around the external surface 74 of tulip housing 4 such that longitudinally extending protrusions 76 slide into the longitudinally extending indentations 54 of the tulip housing 4. The longitudinally extending protrusions 76, which are located around the diameter, prevent the blade 66 from rotating relative to the tulip housing 4 about all three axes and from translating about all three axes except proximally. Proximal translation is addressed by the axial locking feature discussed below. The longitudinally extending protrusions 76 can be substantially cylindrical, as shown in FIG. 9, or they can have angled longitudinally extending surfaces. In some embodiments, the longitudinally extending protrusions 76 can include at least one flat proximal or distal surface 80 for further restricting axial movement of the blade 66 with respect to the tulip housing 4.

Figure 10:
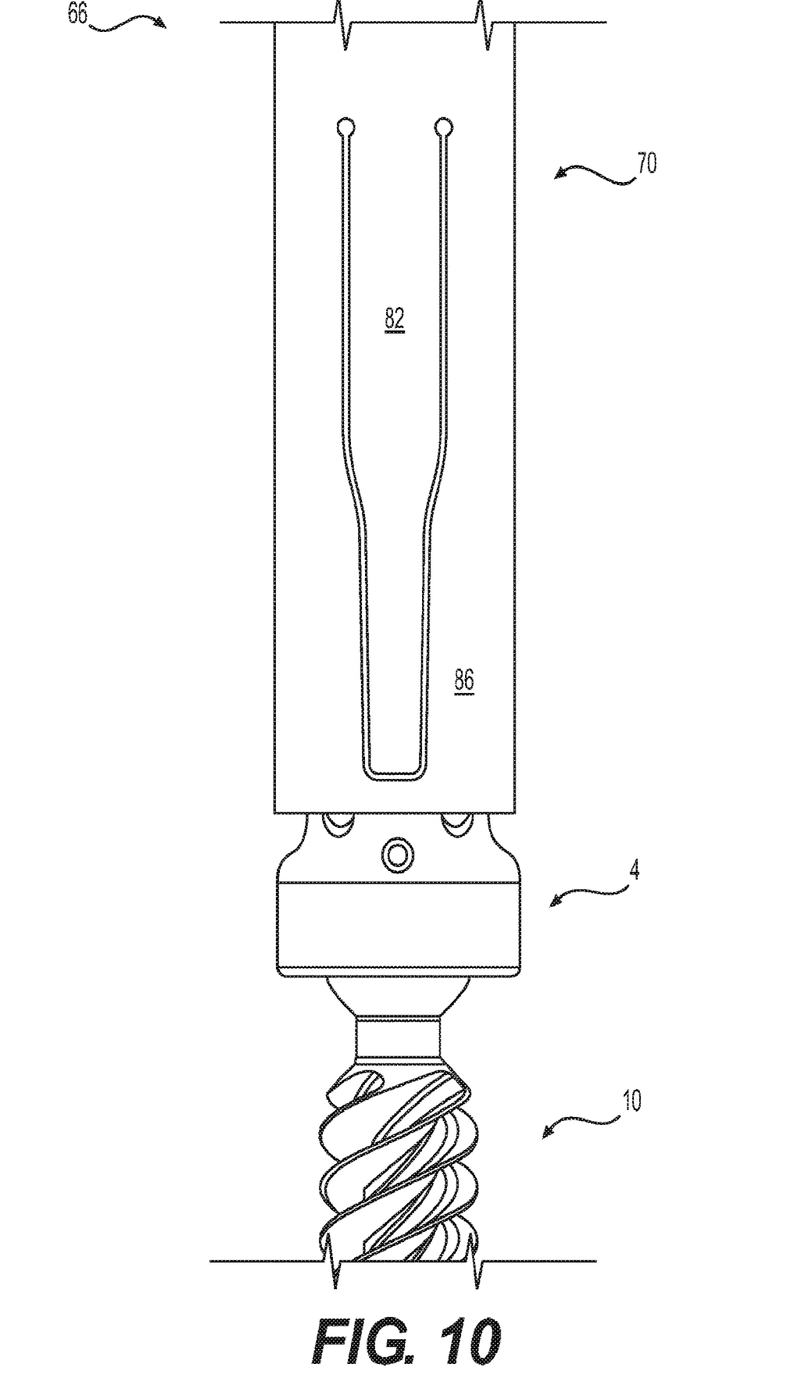
FIG. 10 is a side view of an assembled blade and bone anchor.
Figure 11:
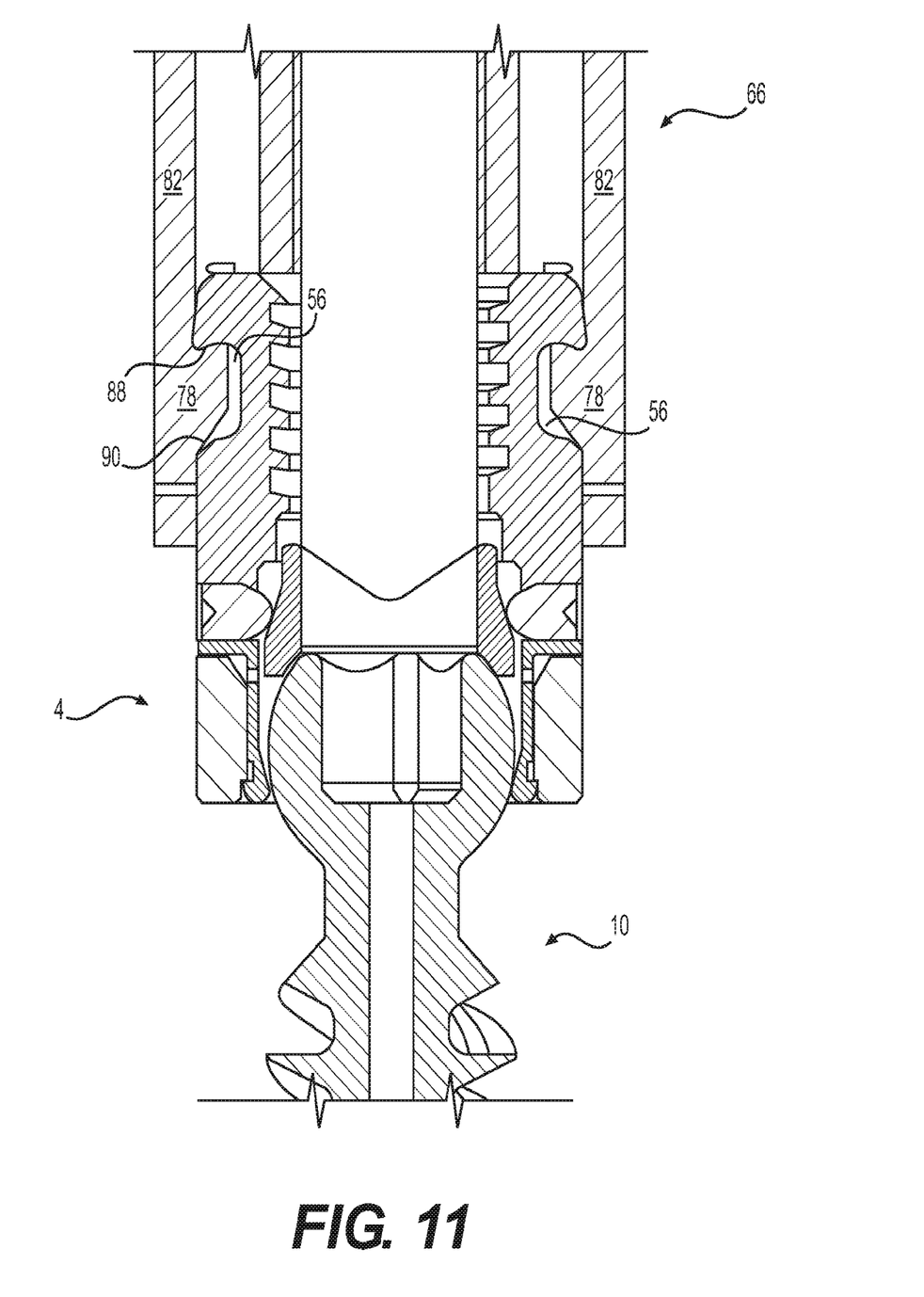
FIG. 11 is a side cross sectional view of an assembled blade and bone anchor.

The curved internal surface 72 can also include an axial locking feature 78, which limits axial movement of the blade with respect to the bone anchor 2. In the embodiment shown in FIG. 9, the axial locking feature is a laterally extending ridge with angled surfaces. The laterally extending ridge 78 is positioned on the inside of distal portion of a living hinge 82, which is an elongated tab cut into the sidewall 84 of blade 66. Living hinge 82 can be seen in totality from the side view of blade 66 shown in FIG. 10, which shows the outer surface 86 of the distal region 70 of blade 66. Living hinge 82 can flex outwardly as blade 66 slides distally over the tulip housing 4, enabling angled surfaces of the laterally extending ridge 78 to catch within the laterally extending indentation 56 of the tulip housing 4 as living hinge 82 returns to its original position (see cross-sectional view in FIG. 11). The proximal surface 88 of the laterally extending ridge 78 creates an acute angle with a sidewall of the living hinge 82. The distal surface 90 of the laterally extending ridge 78 creates an obtuse angle with a sidewall of the living hinge 82. The interaction of the angled surfaces of ridge 78 with the angled surfaces of indentation 56 (the axial locking feature of bone anchor 2) enable the blade 66 to slide over the tulip housing 4 as a distally exerted force is applied (i.e., when blade 66 is pushed inward). However, when the blade is pulled back toward the practitioner, the proximal surface 88 of ridge 78 catches on the distal surface of indentation 56, such that the ridge 78 must be disengaged manually from indentation 56 using a separate disengagement instrument.

In some embodiments, a disengagement instrument can, for example, have two handles with two extensions protruding distally from the handles. The handles and both extensions can be held in an open position by springs, for example. One distally protruding extension contains a pin member which mates with a hole located in the sidewall 84 of blade 66, positioned above the skin of the patient during the procedure. The second distally protruding extension is inserted down the length of the interior portion of the elongated blade 66, and has a projecting member. Compressing the handles thrusts the projecting member outward, thus disengaging the elongated member from the bone anchor (for example, by pushing flexing living hinge 82 outwardly and thereby pushing axial locking feature 78 away from the bone anchor 2). With the handles still compressed, the disengagement instrument holds onto the elongated blade 66 during removal from the surgical site to ensure the elongated blade does not fall back into the surgical site for safety to the patient.

Methods of assembling bone anchors are disclosed herein. The bone anchors disclosed herein are assembled by inserting pressure cap 16 into a through hole 8 at a distal end of a tulip housing 4, inserting a proximal ball head 14 of a bone anchor 2 into the through hole 8 at the distal end of the tulip housing 4, and positioning a retaining ring 20 around a distal radially expandable portion 6 of the tulip housing 4 (thereby preventing distal movement of the pressure cap 16 and the proximal ball head 14 out of the through hole 8). The radially expandable distal portion 6 expands to allow for the passage of pressure cap 16 and ball head 14 as they are inserted into the through hole 8. The expansion is possible because tabs 40 of the radially expandable portion 6 flex outwardly during the passage of the ball head 14 and pressure cap 16, which have larger diameters. Positioning the retaining ring 20 limits further expansion of the distal radially expandable portion 6 of tulip housing 4, preventing distal movement of the ball head 14 out of through hole 8. The method of assembling the bone anchor 2 further comprises activating a compression mechanism that forces the pressure cap 16 into close contact with the ball head 14. In some embodiments, activating a compression mechanism includes inserting a compressing component 24 through a sidewall 28 of the metal tulip housing 4.

The bone anchors described herein can be inserted without tapping or undertapping. Methods of inserting the bone anchors include inserting a bone access needle into a bone to create a needle hole space, inserting a guidewire through the bone access needle within the needle hole space, removing the bone access needle, screwing a cannulated bone anchor into the needle hole space over the guidewire, and removing the guidewire. No tapping or undertapping steps are performed, reducing the duration and the invasiveness of the procedure. In some embodiments of the method, the bone anchor is screwed into the needle hole space without first widening the needle hole space. In other embodiments, the needle hole space is widened to create a pilot hole prior to screwing in the bone anchor. The bone can be a pedicle in some embodiments. The bone access needle can be a pedicle access needle, or, in some embodiments, a Jamshidi needle. The minor diameter of the distal threaded portion 12 of the bone anchor 2 can be chosen to approximately match the outer diameter of the bone access needle (and therefore, the needle hole space). The method of inserting the bone anchor can also include inserting a spinal rod 3 between the sidewalls 30 of two adjacent tulip housings 4, and locking the spinal rod 3 into place using set screws 5 (an exploded perspective view of these components is shown in FIG. 1).

What is claimed is:

1. An elongated blade that is configured to connect to a tulip housing that is in turn connected to a head portion of a bone anchor; said elongated blade comprises first and second blade members; said first and second blade members are spaced apart from one another along a majority of a longitudinal length of said elongated blade; each of said first and second blade members includes first and second rotational locking features that are spaced apart from one another; each of said first and second rotational locking features is positioned on an interior surface of each of said first and second blade members and extends toward a central axis of said elongated blade; each of said first and second rotational locking features has a substantially cylindrical shape; each of said first and second blade members includes an axial locking feature that is positioned between said first and second rotational locking features; each of said axial locking features is positioned on an interior surface of each of said first and second blade members and extends toward said central axis of said elongated blade; each of said axial locking features is positioned on a living hinge that is formed in said first and second blade members; each of said first and second rotational locking features has a longitudinal length along a longitudinal axis of said elongated blade that is greater than a longitudinal length of each of said axial locking features along said longitudinal axis of said elongated blade; each of said first and second rotational locking features has a longitudinal axis that is parallel to said central axis of said elongated blade; and     wherein each of said rotational locking features on each of said first and second blade members is configured to limit rotational movement of said elongated blade relative to the tulip housing when said rotational locking features are in engagement with the tulip housing; and     wherein said axial locking feature on each of said first and second blade members is configured to limit axial movement of said elongated blade relative to the tulip housing when said axial locking features are in engagement with the tulip housing; and     wherein said first and second blade members each have an exterior surface that has a curved shaped; said interior surface of each of said first and second blade members has a curved shape; each of said first and second blade members has a mirrored shape from another; and     wherein said living hinge on each of said first and second blade members has a narrow width portion and wide width portion; said narrow width portion is positioned below said wide width portion; an interior surface of said narrow width portion fully includes said axial locking feature.

2. The elongated blade as defined in claim 1, wherein said axial locking feature on each of said first and second blade members includes an upper interior face portion and a lower interior face portion; said upper interior face portion lies in a plane that is parallel to said central axis of said elongated blade; said lower interior face portion slopes inwardly from said upper interior face portion.

3. The elongated blade as defined in claim 2, wherein each of said first and second blade members includes a plurality of protrusions that are located between a proximal end of said elongated blade and said living hinge on each of said first and second blade members.

4. The elongated blade as defined in claim 1, wherein each of said first and second blade members is formed of Mo—Re alloy.

5. The elongated blade as defined in claim 3, wherein each of said first and second blade members is formed of Mo—Re alloy.

6. A method for securing said elongated blade as defined in claim 1 to the tulip housing comprising:

sliding said first and second rotational locking features on each of said first and second blade members into longitudinal cavities in said tulip housing; said tulip housing includes four of said longitudinal cavities; each of said longitudinal cavities having a partial cylindrical shape along a longitudinal length of each of said longitudinal cavities; each of said longitudinal cavities has a side opening that opens to an exterior side of said tulip housing;

causing said axial locking feature on each of said first and second blade members to engage axial cavities in said tulip housing; said tulip housing includes two of said axial cavities; each of said axial cavities is positioned between a pair of said longitudinal cavities; at least a portion of said axial locking feature on each of said first and second blade members is positioned in said axial cavity when said axial locking feature engages said axial cavity; and     wherein rotational movement of said elongated blade relative to said tulip housing is limited when said first and second rotational locking features on each of said first and second blade members are positioned in said longitudinal cavities in said tulip housing; and     wherein axial movement of said blade relative to said tulip housing is limited when said axial locking feature on each of said first and second blade members are positioned in said axial cavities in said tulip housing.

7. A method for securing said elongated blade as defined in claim 5 to the tulip housing comprising:

sliding said first and second rotational locking features on each of said first and second blade members into longitudinal cavities in said tulip housing; said tulip housing includes four of said longitudinal cavities; each of said longitudinal cavities having a partial cylindrical shape along a longitudinal length of each of said longitudinal cavities; each of said longitudinal cavities has a side opening that opens to an exterior side of said tulip housing;

causing said axial locking feature on each of said first and second blade members to engage axial cavities in said tulip housing; said tulip housing includes two of said axial cavities; each of said axial cavities is positioned between a pair of said longitudinal cavities; at least a portion of said axial locking feature on each of said first and second blade members is positioned in said axial cavity when said axial locking feature engages said axial cavity; and     wherein rotational movement of said elongated blade relative to said tulip housing is limited when said first and second rotational locking features on each of said first and second blade members are positioned in said longitudinal cavities in said tulip housing; and     wherein axial movement of said blade relative to said tulip housing is limited when said axial locking feature on each of said first and second blade members are positioned in said axial cavities in said tulip housing.

\* \* \* \* \*